United States Patent [19]

Herrmann et al.

[11] Patent Number: 5,240,000
[45] Date of Patent: Aug. 31, 1993

[54] TARGETING DEVICE FOR A LITHOTRITOR

[75] Inventors: Bernhard Herrmann, Germering; Jürgen Neumann, Alling, both of Fed. Rep. of Germany

[73] Assignee: Dornier Medizintechnik GmbH, Fed. Rep. of Germany

[21] Appl. No.: 780,115

[22] Filed: Oct. 21, 1991

[30] Foreign Application Priority Data

Oct. 20, 1990 [DE] Fed. Rep. of Germany ....... 4033439

[51] Int. Cl.$^5$ .......................... A61B 5/05; A61H 1/00
[52] U.S. Cl. .............................. 128/653.1; 128/24 EL
[58] Field of Search ................ 128/653.1, 24 EL, 659, 128/653.5; 606/127, 128; 378/62, 162, 205, 147

[56] References Cited

FOREIGN PATENT DOCUMENTS 4033439 10/1990 Fed. Rep. of Germany .

Primary Examiner—Lee S. Cohen
Assistant Examiner—Marianne Parker
Attorney, Agent, or Firm—Evenson, McKeown, Edwards & Lenahan

[57] ABSTRACT

A targeting device for x-ray locating during an extracorporeal treatment of patients with focused shock waves, particularly for a lithotritor, is suggested. The targeting device comprises a carrier on or in which x-ray positive elements, preferably metal wires, are arranged such that they point to the focal point of the shock wave system. In the x-ray image, the position of the elements clearly indicates the position of the focal point.

17 Claims, 3 Drawing Sheets

TARGETING DEVICE FOR A LITHOTRITOR

BACKGROUND AND SUMMARY OF THE INVENTION

This invention relates to a targeting device for x-ray locating during the extracorporeal treatment of patients with focused shock waves, particularly for a lithotritor.

Non-invasive lithotrity with focussed shock waves requires the precise locating of the stone and a precise positioning of the patient with respect to the focal point in which the shock waves meet.

So far, x-ray locating and the locating of ultrasonic devices have been used (German Patent Document DE-PS 34 26 398). While the ultrasonic locating can be carried out continuously, a permanent "x-ray filming" is eliminated because of the radiation stress. On the other hand, not all types of stones can be sufficiently imaged by the ultrasonic device.

From the German Patent Document DE-PS 39 19 083, corresponding to U.S. Pat. No. 5,070,861 to Einars et al., a targeting device for x-ray locating is known in the case of an extracorporeal treatment of patients with focussed shock waves, particularly for a lithotritor, which has a carrier which is made of an x-ray negative material, can be fastened to the shock wave source and carries at least four x-ray positive reference points of which at least two are situated on a first straight line which leads through the focal point of the shock waves and of which at least two others are situated on a second straight line which also leads through the focal point of the shock waves.

When this targeting device is used according to the "notch-and-bead principle", the x-ray C-arc must be brought into two specific discrete positions. A targeting device would be desirable which indicates the focal point in any arbitrary position of the x-ray C-arc.

It is therefore an object of the invention to provide another targeting device by means of which the focal point of the therapy unit is also visible without any rough adjusting of the x-ray C-arc.

This object is achieved by a targeting device wherein the x-ray positive elements are straight-lined and are arranged on straight lines which intersect in the focal point of the shock wave system.

By means of the targeting device according to the invention, a positioning can take place by means of an x-ray C-arc which comprises an x-ray tube and an image enhancer opposite the x-ray tube, with a few images and irrespective of the position of the x-ray C-arc since the focal point can be recognized on every x-ray image.

As the "vanishing point" of the straight elements, the focal point is easily recognizable on every x-ray image which reduces the number of images to be taken. In preferred embodiments, three or four elements are used. This number is sufficient for obtaining clear results.

An x-ray negative material, such as the synthetic material Delrin, is considered for the carrier. If possible, the carrier should not be visible on the projecting screen. The mass distribution perpendicularly to the irradiation direction should be as homogenous as possible. The outer contour should be body-friendly on the side facing the patient; that is, it should have no sharp edges. It should be as simple as possible to fasten the carrier to the shock wave source and to remove it again, and the carrier should be so sturdy that the targeting direction under a load of approximately 30 kg deforms only to such an extent that a displacement of the straight target line remains in the millimeter range. Such a load may occur when the targeting apparatus bumps against the patient's body.

The reference elements should be made of a material that is as x-ray positive as possible and is rich in contrasts on the projecting screen. Suitable materials are all metals, particularly those with a high atomic number, such as steel, lead or soldering tin with a high lead content.

The carrier may have the shape of a hollow body, such as a cylinder. The x-ray positive elements will then, for example, be tensioned steel wires. Other shapes are also possible, such as the shape of a truncated cone or that of a cone, on the corresponding shell surfaces of which the metallic x-ray positive elements are arranged. All carriers have in common that the x-ray positive elements all extend toward a point outside the carrier which is the focal point of the shock wave source.

Other objects, advantages and novel features of the present invention will become apparent from the following detailed description of the invention when considered in conjunction with the accompanying drawings.

DETAILED DESCRIPTION OF THE DRAWINGS

Figure 1:
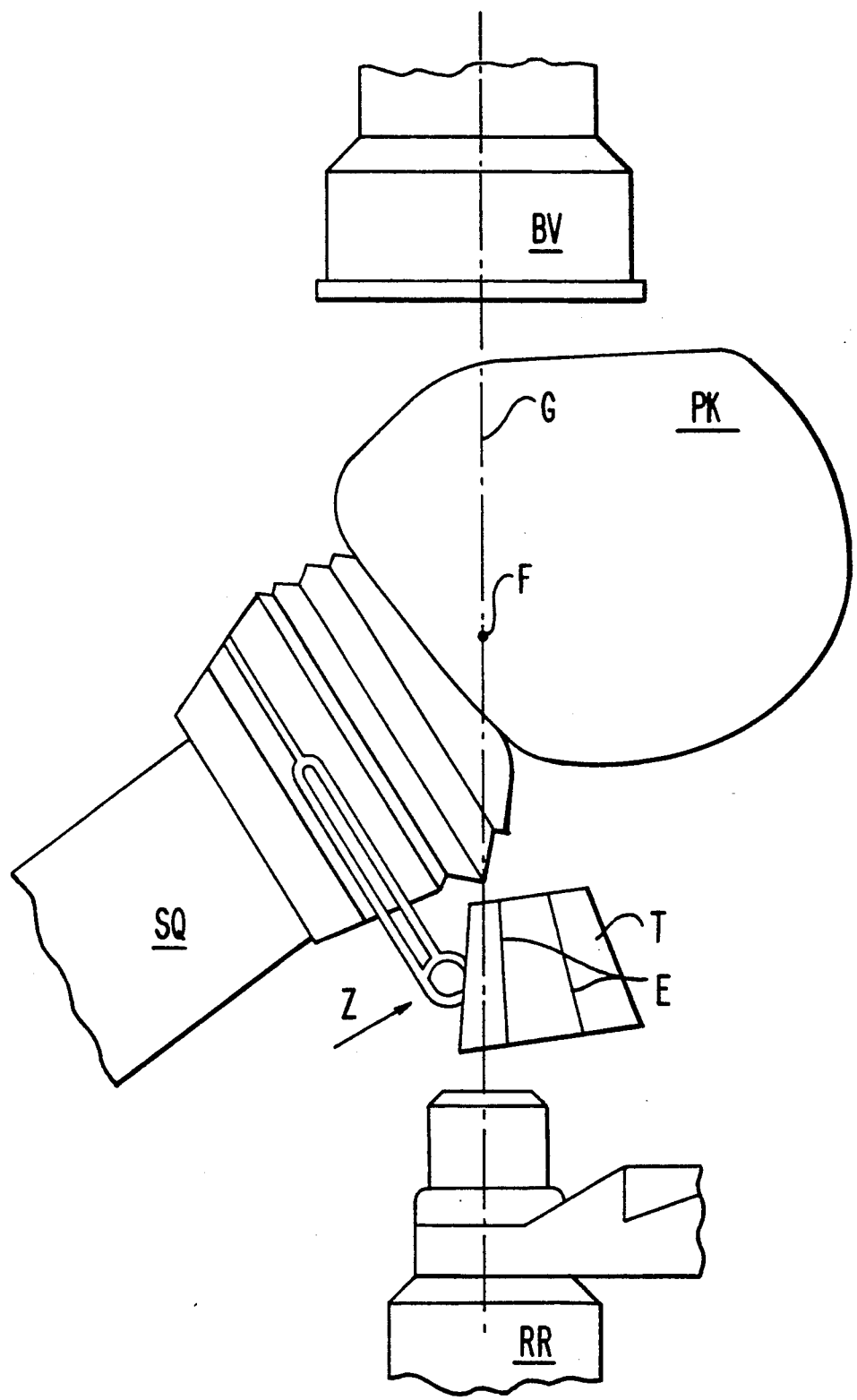
FIG. 1 is a schematic view of the targeting device according to the invention.

FIG. 1 illustrates a patient's body PK which is arranged on a couch, which is not shown, within an x-ray C-arc. The x-ray C-arc comprises an x-ray tube RR on the bottom and an image enhancer BV on the top which are arranged colinearly (principal axis G). The x-ray C-arc can be swivelled about an axis which is situated approximately in parallel with respect to the longitudinal axis of the patient's body. On the patient's body PK, a shock wave source SQ is disposed which, in this case, on its front side, is closed off by an elastic flexible bellows. The shock wave source SQ generates shock waves, focusses them, and guides them to a focal point—focal point F. In this case, the targeting device Z according to the invention is fastened to the shock wave source SQ and comprises the truncated-cone-shaped or conical carrier T, on the shell surface of which the x-ray positive elements E (metal wires, metal foils) are arranged. The elements E are straight, elongated and are situated on straight lines which extend through the focal point F of the shock wave source SQ.

Figure 2:
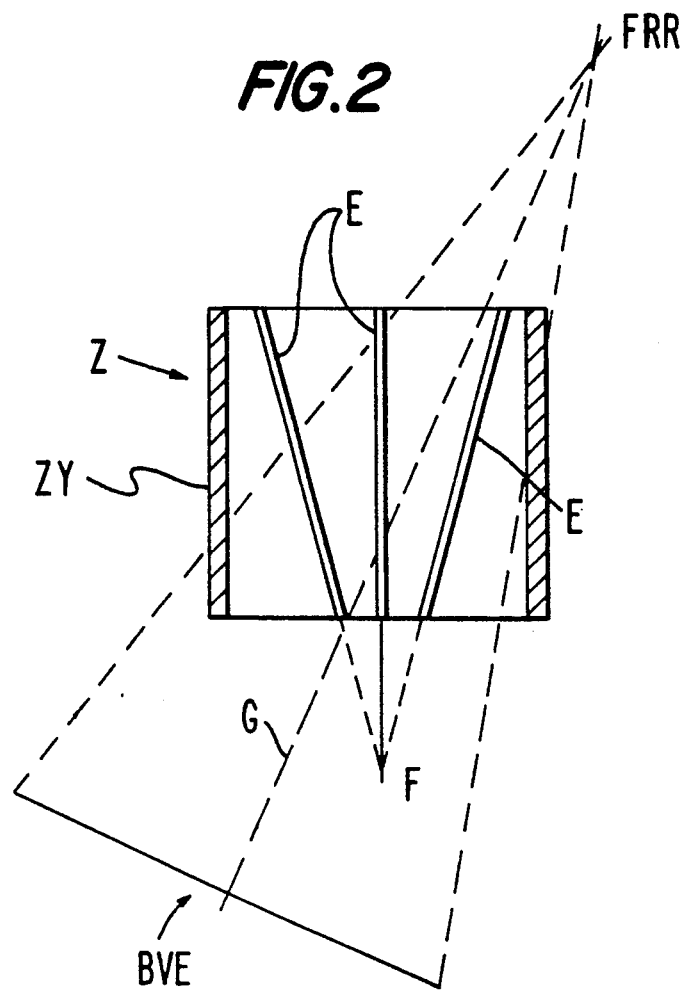
FIG. 2 is a schematic view depicting another embodiment of a targeting device, shown in a first position.
Figure 2A:
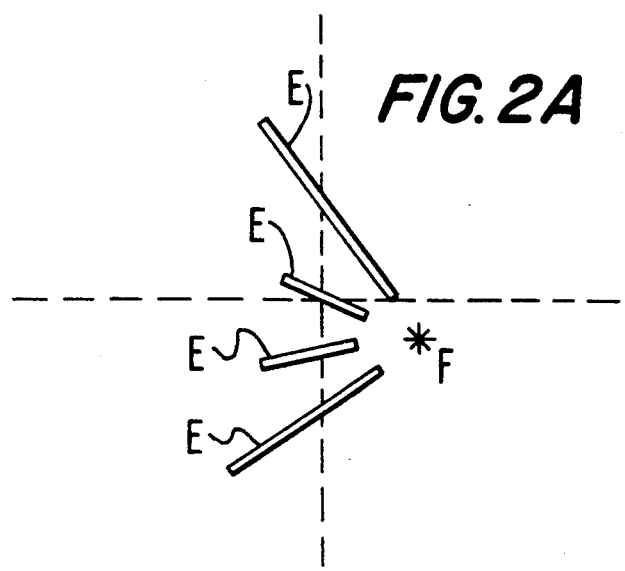
FIG. 2A is a view of an x-ray monitoring screen representing the FIG. 2 position of the target elements and shock wave source focal point.
Figure 3:
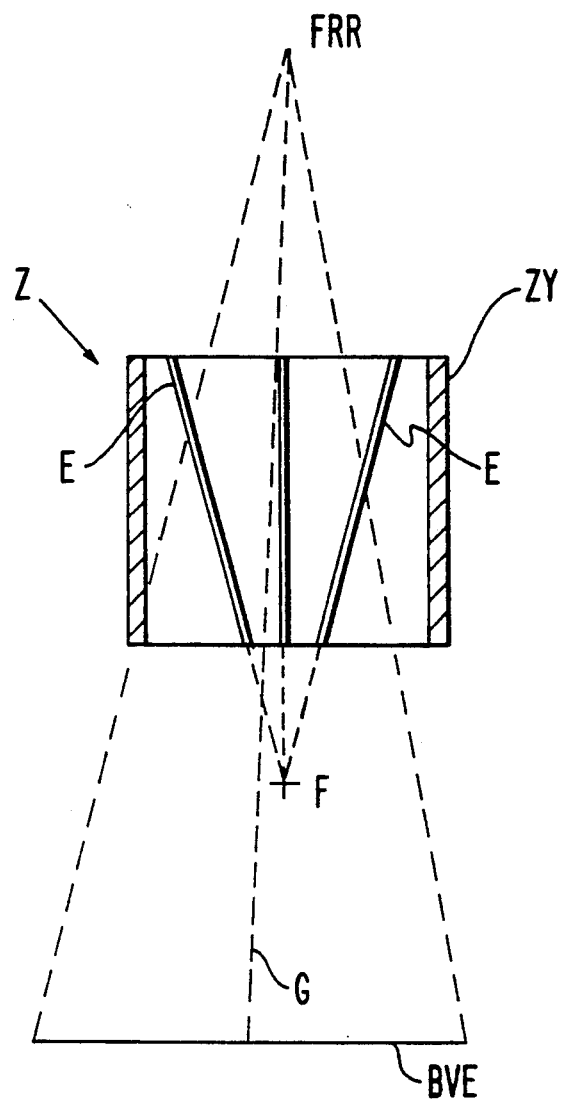
FIG. 3 is a schematic view of the embodiment of FIG. 2, shown in another position.
Figure 3A:
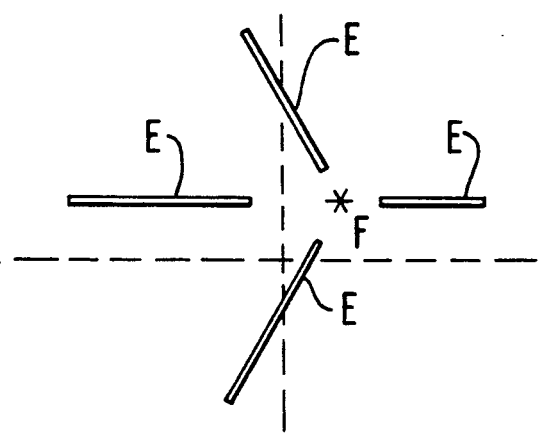
FIG. 3A is a view of an x-ray monitoring screen representing the FIG. 3 position of the target elements and shock wave source focal point in the FIG. 3 orientation.

FIGS. 2, 2A and 3, 3A show another embodiment of a targeting element Z. In this case, the carrier is constructed as a cylinder Zy, inside which four metal wires are tensioned as the x-ray positive elements E, which are all disposed on straight lines which extend through the focal point F of the shock wave source SQ. As part of the x-ray system, the focal point FRR of the x-ray tube RR, the principal axis G, and the focal plane BVE of the image enhancer BV are illustrated. In FIGS. 2A and 3A, the corresponding image is, in each case, entered on the x-ray monitor (focal plane BVE). It can be recognized that the images of the four elements E always clearly point to the focal point F of the shock wave system SQ that is to be determined.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. A targeting system for x-ray locating during the extracorporeal treatment of patients with focused shock waves, said targeting system comprising:
    a carrier which is made of an x-ray negative material,
    a fastener means for fastening the carrier to a shock wave source,
    a plurality of x-ray positive elements carried by the carrier, and
    x-ray monitor means for monitoring the position of the x-ray positive elements and of a focal point of the shock wave source,
    wherein the x-ray positive elements are straight-lined and are arranged on straight lines which intersect in the focal point of the shock wave source, whereby the x-ray monitor means include a continuous display with the straight-lined x-ray positive elements pointing toward the focal point of the shock wave source.

2. A targeting system according to claim 1, wherein three x-ray positive elements are provided.

3. A targeting system according to claim 2, wherein the x-ray positive elements are formed by tensioned metal wires.

4. A targeting system according to claim 3, wherein the metal wires are tensioned inside a cylinder.

5. A targeting system according to claim 2, wherein the x-ray positive elements are made of metal and are arranged on a truncated-cone-shaped carrier.

6. A targeting system according to claim 2, wherein the x-ray positive elements are made of metal and are arranged on a conical carrier.

7. A targeting system according to claim 1, wherein the x-ray positive elements are formed by tensioned metal wires.

8. A targeting system according to claim 7, wherein the metal wires are tensioned inside a cylinder.

9. A targeting system according to claim 7, wherein said metal wires are steel wires.

10. A targeting system according to claim 9, wherein the metal wires are tensioned inside a cylinder.

11. A targeting system according to claim 1, wherein the x-ray positive elements are made of metal and are arranged on a truncated-cone-shaped carrier.

12. A targeting system according to claim 1, wherein four x-ray positive elements are provided.

13. A targeting system according to claim 12, wherein the x-ray positive elements are formed by tensioned metal wires.

14. A targeting system according to claim 13, wherein the metal wires are tensioned inside a cylinder.

15. A targeting system according to claim 12, wherein the x-ray positive elements are made of metal and are arranged on a truncated-cone-shaped carrier.

16. A targeting system according to claim 12, wherein the x-ray positive elements are made of metal and are arranged on a conical carrier.

17. A targeting system according to claim 1, wherein the x-ray positive elements are made of metal and are arranged on a conical carrier.

* * * * *